United States Patent
Nempont et al.

(10) Patent No.: US 11,291,424 B2
(45) Date of Patent: Apr. 5, 2022

(54) DEVICE AND A CORRESPONDING METHOD FOR PROVIDING SPATIAL INFORMATION OF AN INTERVENTIONAL DEVICE IN A LIVE 2D X-RAY IMAGE

(71) Applicant: KONINKLIJKE PHILIPS N.V., Eindhoven (NL)

(72) Inventors: Olivier Pierre Nempont, Suresnes (FR); Pascal Yves Francois Cathier, Asnieres-sur-Seine (FR); Raoul Florent, Ville D'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 234 days.

(21) Appl. No.: 16/615,510

(22) PCT Filed: May 23, 2018

(86) PCT No.: PCT/EP2018/063431
§ 371 (c)(1),
(2) Date: Nov. 21, 2019

(87) PCT Pub. No.: WO2018/215499
PCT Pub. Date: Nov. 29, 2018

(65) Prior Publication Data
US 2020/0085398 A1 Mar. 19, 2020

(30) Foreign Application Priority Data
May 24, 2017 (EP) ..................................... 17305614

(51) Int. Cl.
*A61B 6/12* (2006.01)
*A61B 8/12* (2006.01)
(Continued)

(52) U.S. Cl.
CPC .............. *A61B 6/5247* (2013.01); *A61B 6/12* (2013.01); *A61B 6/4417* (2013.01); *A61B 6/463* (2013.01);
(Continued)

(58) Field of Classification Search
CPC ....... A61B 6/5247; A61B 6/12; A61B 6/4417; A61B 6/463; A61B 6/486; A61B 8/0841;
(Continued)

(56) References Cited

U.S. PATENT DOCUMENTS 10,157,491 B2 * 12/2018 Florent .................. A61B 8/483
10,515,449 B2 * 12/2019 Miao ........................ A61B 8/12
(Continued)

FOREIGN PATENT DOCUMENTS

WO 2011070477 A1 6/2011
WO 2014102718 A1 7/2014

OTHER PUBLICATIONS

PCT/EP2018/063431 ISR & WO, Aug. 2, 2018, 12 Page Document.

*Primary Examiner* — Colin T. Sakamoto (57) ABSTRACT

The present invention relates to displaying spatial information of an interventional device in a live 2D X-ray image. In order to provide a facilitated visualization technique to provide 3D information of a subject, a device (10) for providing spatial information of an interventional device in a live 2D X-ray image is provided. The device comprises an input unit (12), and a processing unit (16). The input unit is configured to provide an actual 2D X-ray image (18) of a region of interest related to a portion of a patient's body. A target location (22) lies within the region of interest. At least a portion (20) of an interventional device is arranged in the region of interest. The input unit is configured to provide actual 3D ultrasound data of at least a part of the region of interest and at least a portion of an interventional device
(Continued)

(19). The target location (22) lies within the region of interest. The processing unit is configured to register the actual 3D ultrasound data to the actual 2D X-ray image. The processing unit is also configured to identify the target location in the 3D ultrasound data, and to determine, based on the actual 3D ultrasound data, a spatial relation between the portion of the interventional device and the target location, to retrieve a distance value in a projection direction of the actual 2D X-ray image from the spatial relation, and, based on the distance value, to generate a graphical representation (32) indicative of the spatial relation, the graphical representation to be displayed with the actual 2D X-ray image.

14 Claims, 4 Drawing Sheets

(51) Int. Cl.
| | | |
|---|---|---|
| *G06T 15/20* | (2011.01) | |
| *G06T 7/174* | (2017.01) | |
| *A61B 6/00* | (2006.01) | |
| *A61B 8/08* | (2006.01) | |
| *A61B 8/00* | (2006.01) | |

(52) U.S. Cl.
CPC .............. *A61B 6/486* (2013.01); *A61B 6/503* (2013.01); *A61B 8/0841* (2013.01); *A61B 8/0883* (2013.01); *A61B 8/12* (2013.01); *A61B 8/463* (2013.01); *A61B 8/466* (2013.01); *A61B 8/483* (2013.01); *A61B 8/5261* (2013.01); *G06T 7/174* (2017.01); *G06T 15/205* (2013.01); *G06T 2207/10116* (2013.01); *G06T 2207/10136* (2013.01); *G06T 2207/30048* (2013.01); *G06T 2207/30204* (2013.01); *G06T 2210/41* (2013.01)

(58) Field of Classification Search
CPC ........... A61B 8/12; A61B 8/463; A61B 8/466; A61B 8/483; A61B 8/5261; G06T 7/174; G06T 15/205; G06T 2207/10116; G06T 2207/10136; G06T 2207/30204; G06T 2210/41
See application file for complete search history.

(56) References Cited

U.S. PATENT DOCUMENTS

| | | | |
|---|---|---|---|
| 2002/0045817 A1* | 4/2002 | Ichihashi | A61B 6/4233 600/425 |
| 2006/0153468 A1* | 7/2006 | Solf | A61B 34/20 382/254 |
| 2007/0021668 A1* | 1/2007 | Boese | A61B 90/36 600/424 |
| 2008/0283771 A1 | 11/2008 | Li | |
| 2009/0088830 A1 | 4/2009 | Mohamed et al. | |
| 2010/0111389 A1* | 5/2010 | Strobel | A61B 6/12 382/131 |
| 2010/0256510 A1* | 10/2010 | Leiblein | A61B 90/37 600/509 |
| 2011/0112398 A1* | 5/2011 | Zarkh | A61B 6/503 600/424 |
| 2012/0123250 A1 | 5/2012 | Pang et al. | |
| 2014/0275985 A1* | 9/2014 | Walker | A61B 6/485 600/424 |
| 2017/0095296 A1 | 4/2017 | Olivan Bescos et al. | |

\* cited by examiner

DEVICE AND A CORRESPONDING METHOD FOR PROVIDING SPATIAL INFORMATION OF AN INTERVENTIONAL DEVICE IN A LIVE 2D X-RAY IMAGE

CROSS-REFERENCE TO PRIOR APPLICATIONS

This application is the U.S. National Phase application under 35 U.S.C. § 371 of International Application No. PCT/EP2018/063431, filed on May 23, 2018, which claims the benefit of European Patent Application No. 17305614.4, filed on May 24, 2017. These applications are hereby incorporated by reference herein.

FIELD OF THE INVENTION

The present invention relates to a device for providing spatial information of an interventional device in a live 2D X-ray image, to an X-ray imaging system, to a method for providing spatial information of an interventional device in a live 2D X-ray image, to a computer program element for controlling such a device and to a computer readable medium having stored the program element.

BACKGROUND OF THE INVENTION

In X-ray guided interventions, fluoroscopy may be used to navigate a tool towards its target during intervention. Fluoroscopy is an imaging technique that uses X-rays to be able to obtain real-time moving images of an object. In particular, inserted interventional devices that are not visible by human eyesight are made visible in relation to the object.

For achieving depth information, additional X-ray images are required, such as bi-plane imaging. However, this may be cumbersome and may result in additional X-ray radiation.

Alternatively, a second imaging modality may be used, such as 3D ultrasound imaging. WO 2011/070477 A1 describes a combined X-ray and ultrasound imaging system, in which 3D ultrasound imaging data may, in real time, supplement the X-ray images. In addition to providing depth information, the ultrasound data may render visible structures with low X-ray visibility, such as soft tissue.

SUMMARY OF THE INVENTION

There may thus be a need to provide a facilitated visualization technique to provide 3D information of a subject.

The object of the present invention is solved by the subject-matter of the independent claims; further embodiments are incorporated in the dependent claims. It should be noted that the following described aspects of the invention apply also for the device for providing spatial information of an interventional device in a live 2D X-ray image, for the X-ray imaging system, for the method for providing spatial information of an interventional device in a live 2D X-ray image, for the computer program element for controlling such a device and also for the computer readable medium having stored the program element.

According to a first aspect, a device for providing spatial information of an interventional device in a live 2D X-ray image is provided. The device comprises an input unit and a processing unit. The input unit is configured to provide a live 2D X-ray image of a region of interest related to a portion of the patient's body. A target location lies within the region of interest. The input unit is further configured to provide live 3D ultrasound data of at least a part of the region of interest and at least a portion of an interventional device. The processing unit is configured to register the live 3D ultrasound data to the live 2D X-ray image. The processing unit is configured to identify the target location in the 3D ultrasound data, and to determine, based on the live 3D ultrasound data, a spatial relation between the portion of the interventional device and the target location. The processing unit is configured to generate a graphical representation indicative of the spatial relation. The graphical representation is provided to be displayed with the live 2D X-ray image.

As an exemplary embodiment of this first aspect, a device for providing spatial information of an interventional device in a live 2D X-ray image is provided. The device comprises an input unit and a processing unit. The input unit is configured to provide an actual (or live, or current) 2D X-ray image of a region of interest related to a portion of the patient's body. A target location lies within the region of interest. At least a portion of an interventional device is arranged in the region of interest. The input unit is further configured to provide actual (or live, or current) 3D ultrasound data of at least the part of the region of interest and at least the portion of the interventional device. The target location lies within the region of interest. The processing unit is configured to register the actual 3D ultrasound data to the actual 2D X-ray image. The processing unit is configured to identify the target location in the 3D ultrasound data, and to determine, based on the actual 3D ultrasound data, a spatial relation between the portion of the interventional device and the target location. The processing unit is also configured to retrieve a distance value in a projection direction of the actual 2D X-ray image from the spatial relation. The processing unit is configured to generate, based on the distance value, a graphical representation indicative of the spatial relation. The graphical representation is provided to be displayed with the actual 2D X-ray image. The graphical representation is thus displayable with the actual 2D X-ray image.

The term "patient" refer to a subject that is undergoing e.g. an interventional procedure or examination. The patient could also be referred to as "subject" or "individual". The individual, i.e. subject, is thus the object of interest for the procedure.

In an example, the input unit provides the actual 2D X-ray image and the actual 3D ultrasound data.

The term "arranged in" refers to the device being present in the region of interest at least with a portion. The device is thus located or provided in the region of interest. In an example of the device being a catheter, guide wire, needle or the like, the device is inserted such that e.g. the tip, or any other predetermined portion, of the device is within the region of interest, i.e. in the field of view covered by the 2D and the 3D image data, i.e. the 2D X-ray image and the 3D ultrasound data.

As, in an example, the 2D X-ray image and the 3D ultrasound data are referring to the same actual point or instance in time, or time range or time-period, the respective 2D and 3D data shows the same region of interest, just with different data information due to different image data acquisition techniques. Hence, the interventional device being arranged e.g. with a tip portion in the region of interest will be present in both 2D and 3D data.

In an example, the region of interest is a portion of a patient's body, in which a user is navigating the interventional device to the target location. A predetermined point of the interventional device is to be navigated to a target location. For example, a tip portion is to be navigated to the target location. In a further example, a shaft or side portion is to be navigated to the target location.

In an example, the region of interest (as provided by the actual X-ray image) shows the predetermined point of the interventional device, i.e. the interventional device is moved such that the predetermined point of the interventional device is arranged within the region of interest.

In an example, the processing unit is configured to provide image data for displaying the actual 2D X-ray image and the graphical representation.

In an example, the portion of the interventional device relates to a part of the interventional device with a point or portion that is to be navigated to the target. The portion of the interventional device thus comprises a predetermined point of the interventional device.

In an example, the 3D ultrasound data comprises 3D ultrasound data of the predetermined point of the interventional device, i.e. the interventional device is moved such that the predetermined point of the interventional device is arranged within the part that is covered by the ultrasound data.

The target location is also referred to as a predetermined location defined as target or target position. In an example, the user is navigating a predetermined point of the interventional device to the predetermined target location.

The term, "indicative" refers to a representation that allows the user to perceive the actual distance in a preferably facilitated manner.

In an example, the graphical representation is based on the spatial relation.

In an example, the graphical representation is displayed with the actual 2D X-ray image.

In an example, the term "to identify" relates to determining the target location in the 3D ultrasound data. This may be provided manually by the user. In another example, this is provided by The term "actual" refers to a current situation, in which the 2D X-ray image and the 3D ultrasound data are acquired.

The term "live" relates to actual (or current) image data. Live, i.e. actual (current), means that any change, i.e. movement of the interventional device is shown instantly on the 2D X-ray image.

The term "navigating" relates to handling the interventional device by a user in a way to arrive at the target location.

In an example, the registration of the current 2D X-ray image and the 3D ultrasound data is provided by registering their respective spatial frames. In an example, the respective image acquisition means are registered to each other. In another example, the registration of the current 2D X-ray image and the 3D ultrasound data is provided by landmarks visible in both image types. In a further option, the registration is provided by the interventional device.

The term "target location" is related to a particular point of interest inside the object. The particular point of interest can be static in the relation of the object, i.e. not moving in relation to the object. In another example, the particular point of interest can be moving with the object, e.g. due to patient motion. In a further example, the particular point of interest can be moving in relation to the object, i.e. moving within the object.

The graphical representation can also be referred as to distance coding. This means that the graphical representation is designed to indicate different depth levels of portion of interventional device in relation to the target location. For example, different colors can be defined for a code pattern.

The 2D X-ray image can also be referred to as projection image of the patient's body in an x-y plane.

The actual 3D ultrasound data can also be referred to as actual 3D ultrasound image data.

The 3D ultrasound data can be related to image data which includes additional spatial information of the acquired image in the z-direction, in addition to spatial information in the x-y plane.

The spatial relation of the point of the interventional device and the targeted location can also be referred to as distance values in x-, y and z-direction.

The distance value in the projection direction of the actual 2D X-ray image could also be referred to as depth or depth value or as a distance value in z-direction of the 2D X-ray image.

In an example, the processing unit is configured to register the actual 3D ultrasound data to a projection direction of the actual 2D X-ray image.

In an example, generating the graphical representation by the processing unit is provided by transforming the distance value into the graphical representation.

In another example, a device for providing spatial information of an interventional device in an actual 2D X-ray image is provided. The device comprises an input unit and a processing unit. The input unit is configured to provide an actual 2D X-ray image of a region of interest related to a portion of a patient's body. A target location lies within the region of interest. The input unit is further configured to provide actual 3D ultrasound data of at least a part of the region of interest and at least a portion of an interventional device. The processing unit is configured to register the actual 3D ultrasound data to the actual 2D X-ray image. The processing unit is also configured to identify the target location in the 3D ultrasound data, and to determine, in case the interventional device is moved such that portion of the interventional device is arranged within the region of interest, based on the actual 3D ultrasound data, a spatial relation between the portion of the interventional device and the target location. The spatial relation is referred to as a depth value or as a distance value in z-direction of the 2D X-ray image. The processing unit is configured to retrieve a distance value in a projection direction of the actual 2D X-ray image from the spatial relation, and to generate a graphical representation based on the distance value, the graphical representation to be displayed with the actual 2D X-ray image.

In an example, the processing unit is configured to determine the spatial relation between the portion of the interventional device and the target location in case the interventional device is moved such that portion of the interventional device is arranged within the region of interest. The spatial relation is a depth value or a distance value in z-direction of the 2D X-ray image. The processing unit is configured to generate a graphical representation based on the distance value.

According to an example, the distance value in the projection direction of the actual 2D X-ray image is a distance value in z-direction of the 2D X-ray image.

The z-direction is perpendicular to the 2D X-ray image plane.

According to an example, the processing unit is configured to generate image data comprising the actual 2D X-ray image and the graphical representation within the actual 2D X-ray image.

According to an example, the graphical representation is a coded graphical representation. In an option, the coded information, such as a color code or pattern code is indicative for a certain relative distance, like too close towards or too far away from the user, or, in viewing direction of the X-ray projection, behind or in front of the plane in which the target is arranged. In another example, the coded information is indicative for a certain absolute distance, like 10 mm behind or 7.5 mm in front of the target plane.

In an example, the coded graphical representation comprises the coded information in form of the color code or pattern code.

According to an example, a display unit is provided that is configured to display the image data comprising the actual 2D X-ray image and the graphical representation within the 2D X-ray image.

According to an example, the processing unit is configured to identify and to visually indicate the target location in the actual 2D X-ray image.

According to an example, the target location is provided with a marker visible in the actual 3D ultrasound data.

Hence, the device can also be referred to as a device for displaying spatial information of an interventional device in a actual 2D X-ray image.

In an example, the 2D X-ray image is shown on a display unit.

In an example, the display unit is a screen.

In an example, the graphical representation is displayed at the target location.

In an example, a predetermined point of the interventional device can be the tip of the interventional device.

In an example, the interventional device is captured both in 2D X-ray and in 3D ultrasound.

In an example, the interventional device can be a transcatheter device.

In an example, the X-ray and interventional ultrasound coordinate systems are registered by a system.

For example, such registration is provided by a system called EchoNavigator® by Philips.

In an example, the target location can be a main vessel of a heart, into which, for example, a stent is going to be placed with the support of the interventional device.

As a result, a visualization technique is provided that brings useful 3D information to the 2D X-ray image without cluttering up the X-ray image. As X-ray image projections do not show "depth" dimension, this dimension in projection direction is now brought back to the X-ray 2D projection image, i.e. the 2D image is enriched or augmented with relative depth information. That means, the user, e.g. an interventionist, may rely on the 2D X-ray image for navigating the interventional device to the target location. By also retrieving a distance value in the projection direction of the interventional device to the target (i.e. target location, target position or target point), or so-called relative depth, from the spatial relation, and transforming the distance value into a graphical representation, a actual 2D X-ray image is generated showing the movement of the interventional device on the 2D X-ray image with additional visual information on the relative depth information without cluttering up the 2D X-ray image. By this, the user can concentrate on the relevant information and is not distracted. Since the additional information is provided by ultrasound, no further X-ray radiation is required.

In a still further example, a device is provided for providing spatial information of an interventional device in a actual 2D X-ray image. The device comprises an input unit and a processing unit. The input unit is adapted to handle several data from different data sources. It is also configured to handle different data types. The input unit is configured to provide an actual 2D X-ray image of a region of interest. The region of interest is related to a portion of the patient's body in which a user is navigating an interventional device. A predetermined point of the interventional device is to be navigated to a predetermined target location within the region of interest. The input unit is further configured to provide actual 3D ultrasound data of at least a part of the region of interest comprising the predetermined point of the interventional device. The processing unit is configured to register the actual 3D ultrasound data to a projection direction of the actual 2D X-ray image. The processing unit is configured to identify the predetermined target location in the 3D ultrasound data, and to determine, based on the actual 3D ultrasound data, a spatial relation between an actual position of the predetermined point of the interventional device and the predetermined target location at least in the projection direction of the actual 2D X-ray image. In an example, the processing unit identifies the predetermined target location by processing a geometrical command from the user, i.e. surgeon before starting the operation. For example, the user transmits the geometrical information of the patient's body via the input unit to the processing unit of the device. In an example, the processing unit determines the distance value between the target location and the portion of the interventional device once the portion of the interventional device is in the region where it can captured by a 3D ultrasound device. In another example, the processing unit determines the distance value between the interventional device and the target location once both lie within the region of interest. The processing unit is configured to retrieve a distance value in the projection direction of the actual 2D X-ray image from the spatial relation, and transforming the distance value into a coded graphical representation. The processing unit is configured to identify and visually indicate the target location in the actual 2D X-ray image. The processing unit is configured to provide image data for displaying the actual 2D X-ray image and the coded graphical representation.

According to a second aspect, an X-ray imaging system is provided for providing spatial information of an interventional device in a live 2D X-ray image. The system comprises an X-ray imaging device, an ultrasound imaging device and a device for providing spatial information of an interventional device in a live 2D X-ray image according to one of the examples above. The X-ray imaging device provides the actual 2D X-ray image, i.e. the actual 2D X-ray image of the region of interest related to the portion of a patient's body, wherein the target location lies within the region of interest, and wherein at least the portion of the interventional device is arranged in region of interest. The ultrasound imaging device provides actual 3D ultrasound data, i.e. the actual 3D ultrasound data of the part of the region of interest and the portion of the interventional device, wherein the target location lies within the region of interest.

In an example, the region of interest is related to a portion of the patient's body in which a user is navigating an interventional device. A predetermined point of the interventional device is to be navigated to a predetermined target location within the region of interest.

The X-ray imaging system can also be referred to as an X-ray imaging system for displaying spatial information of an interventional device in a live 2D X-ray image.

The term "provide" can also be referred to as capture the X-ray image.

In example, the X-ray imaging device provides the actual 2D X-ray image of a region of interest related to a portion of the patient's body in which a user is navigating an interventional device. A predetermined point of the interventional device is to be navigated to a predetermined target location within the region of interest.

According to an example, the ultrasound imaging device is insertable in a patient's body.

In a still further example, a system is provided for providing spatial information of an interventional device in a live 2D X-ray image. The system comprises an X-ray imaging device, an ultrasound imaging device and a device for providing spatial information of an interventional device in a live 2D X-ray image according to the examples above. The X-ray imaging device provides a actual 2D X-ray image of a region of interest. The region of interest is related to a portion of the patient's body in which a user is navigating an interventional device. A predetermined point of the interventional device is to be navigated to a predetermined target location within the region of interest. The ultrasound imaging device provides actual 3D ultrasound data of at least a part of the region of interest comprising the predetermined point of the interventional device.

According to third aspect, a method for providing spatial information of an interventional device in a live 2D X-ray image is provided. The method comprises the following steps:
a) In a first step, an actual 2D X-ray image of a region of interest is provided, being related to a portion of the patient's body, wherein a target location lies within the region of interest. At least a portion of an interventional device is arranged in the region of interest.
b) In a second step, actual 3D ultrasound data of at least a part of the region of interest and at least a portion of an interventional device is provided.
c1) In a third step, the actual 3D ultrasound data is registered to the actual 2D X-ray image.
c2) In a fourth step, the target location in the 3D ultrasound data is identified and the spatial relation between the portion of the interventional device and the target location is determined based on the actual 3D ultrasound data. Further, a distance value in a projection direction of the actual 2D X-ray image is retrieved from the spatial relation.
c3) In fifth step, based on the distance value, a graphical representation indicative of the spatial relation to be displayed with the actual 2D X-ray image is generated.

In an example, a further (sixth) step is provided, also referred to as step d), in which the target location in the actual 2D X-ray image is identified and visually indicated.

In another (seventh) step, also referred to as step e), image data for displaying the actual 2D X-ray image and the graphical representation is provided.

In an example, the region of interest is related to a portion of a patient's body in which a user is navigating an interventional device. For example, a predetermined point of the interventional device is to be navigated to a predetermined target location within the region of interest.

In an example, the region of interest is comprising the predetermined point of the interventional device.

In an example, in step c1), it is provided a step of registering the actual 3D ultrasound data to a projection direction of the actual 2D X-ray image.

In an example, in step c2), it is provided a step of identifying the predetermined target location in the 3D ultrasound data; and determining, based on the actual 3D ultrasound data, a spatial relation between an actual position of the predetermined point of the interventional device and the predetermined target location at least in the projection direction of the actual 2D X-ray image.

The graphical representation may be a coded graphical representation.

In an example, in step e) or following step e), the image data comprising the actual 2D X-ray image and the graphical representation is displayed.

In an example, steps a) to e) are provided in a synchronous continuous manner, such that the user has instant actual data of the area of interest in the patient's body.

In an example, the distance value is determined in 3D ultrasound, e.g. the distance between the point of the interventional device and the target location. For example, the distance value between the point of the interventional device and the target location in the projection direction is computed by subtracting the distance of the point of the interventional device to the X-ray source from the distance of the target location to the X-ray source or vice versa.

In an example, the relative depth is computed as the distance between the target location and a projection of the target point of the interventional device onto a line that goes through both the target and the X-ray imaging device. The projection may, for example, be the standard Euclidean projection of the point of the interventional device.

In another example, the closest point to the line going through the point of the interventional device is provided and aligned with the interventional device, assuming an estimation of the orientation of the interventional device is available additionally to the position of the point of the interventional device.

Hence, the method can also be referred to as a method for displaying spatial information of an interventional device in an actual or live 2D X-ray image.

According to an example, the graphical representation is displayed at the target location.

In an example, a first circle is indicating the target location in the 2D X-ray image, and the first circle changes its color according to a color coding.

In an example, the color coding indicates whether the interventional device is too close or too far from the target location.

According to another example, it is provided a step d) that comprises identifying and visually indicating the position of the interventional device in the actual 2D X-ray image. It is further provided a step e) that comprises that the graphical representation is displayed at the position of the interventional device.

In an option, the graphical representation follows a change of the position of the interventional device within the actual 2D X-ray image.

In a still further example, a method for providing spatial information of an interventional device in a live 2D X-ray image is provided. The method comprises the following steps. In a first step, also referred to as step a), an actual 2D X-ray image of a region of interest is provided, wherein the region of interest is related to a portion of the patient's body in which a user is navigating an interventional device. A predetermined point of the interventional device is to be navigated to the predetermined target location within the region of interest. In a second step, also referred to as step b), actual 3D ultrasound data of at least a part of the region of interest comprising the predetermined point of the interventional device is provided. In a third step, also referred to as step c1), the actual 3D ultrasound data is registered to a projection direction of the actual 2D X-ray image. In a fourth step, also referred to as step c2), the predetermined target location in the 3D ultrasound data is identified and the spatial relation between an actual position of the predetermined point of the interventional device and the predetermined target location at least in a projection direction of the actual 2D X-ray image is determined based on the actual 3D ultrasound data. In a fifth step, also referred to as step c3), a distance value in the projection direction from the spatial relation is retrieved, and the distance value is transformed into a coded graphical representation. In a sixth step, also referred to as step d) the target location in the actual 2D X-ray image is identified and visually indicated. In a seventh step, also referred to as step e), image data for displaying the actual 2D X-ray image and the coded graphical representation is provided.

According to an aspect, it is provided to visualize the distance of an interventional device to a target perpendicular to the actual 2D X-ray image plane by a graphical representation. By this, a user is provided with information about the positioning of the interventional device in the direction perpendicular to the 2D image, which can also be called the depth direction. For example, when navigating an interventional device to a target point, on the actual 2D X-ray image, the user is provided with the position of the interventional device to the target in the 2D plane. The orientation of the interventional device in the depth direction is visualized by a graphical representation, like a circle with a color coding indicating whether the interventional device is far or close to the target point. In addition to the X-ray images, interventional ultrasound thus provides useful additional information relating to the anatomy and the interventional tool in 3D. As a result, a fusion of information relating from X-ray and from interventional ultrasound is achieved. The different geometric natures of these modalities, the former being projective and the latter volumetric, is combined to present the combined or fused information to the user. The 3D information from ultrasound imaging is merged with the projective X-ray image to provide a 2D image (the X-ray projection image) that also comprises 3D information (from the ultrasound).

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
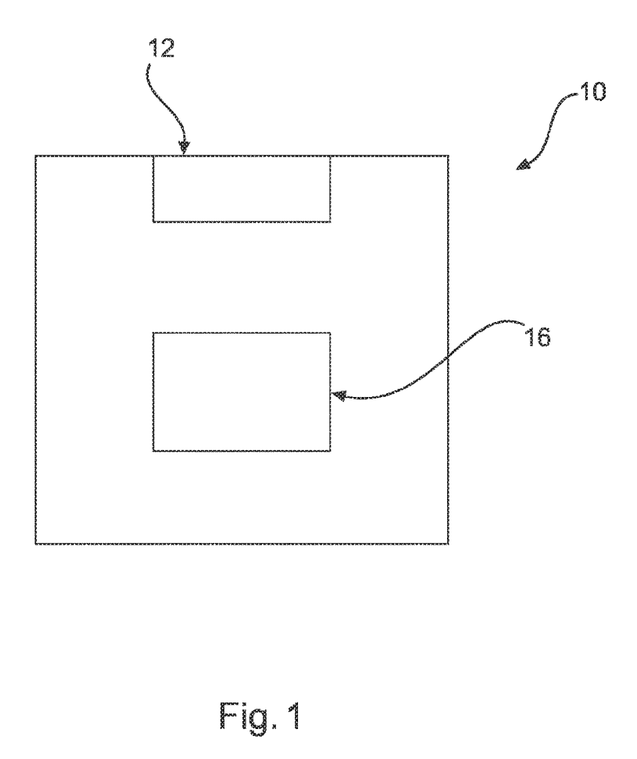
FIG. 1 shows an example of a device for providing spatial information of an interventional device in a live 2D X-ray image.
Figure 2:
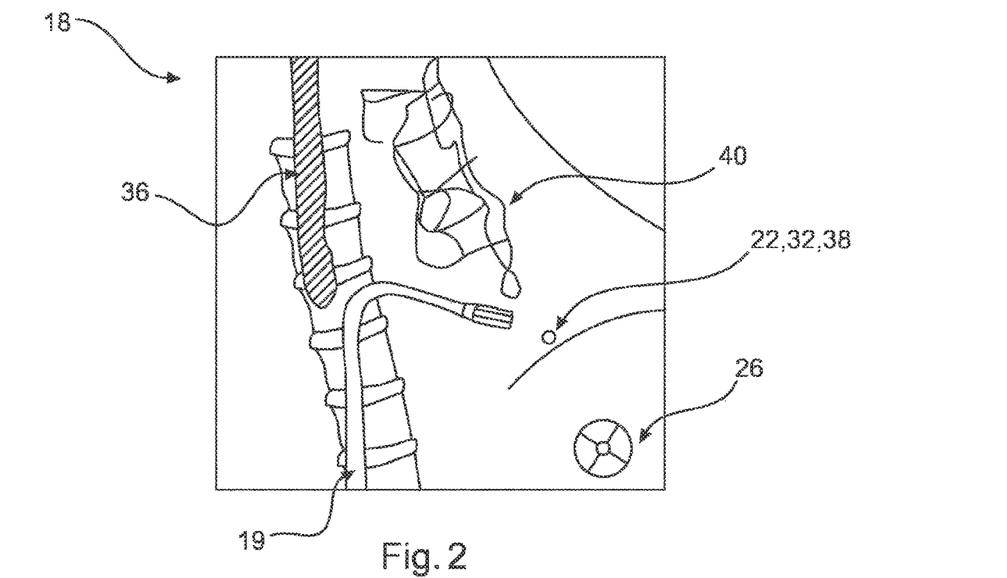
FIG. 2 shows an example of a 2D X-ray image of a region of interest with an interventional device, an ultrasound image device, a target location and a graphical representation.
Figure 3:
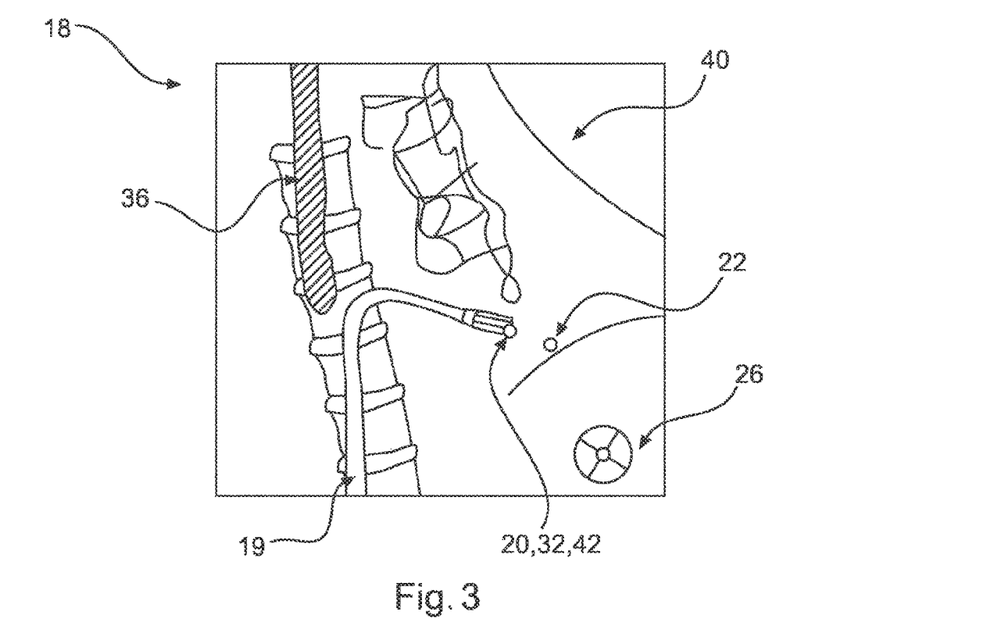
FIG. 3 shows another exemplary illustration of the graphical representation on the actual 2D X-ray image.

FIG. 1 shows a device 10 for displaying spatial information of an interventional device in a 2D projection X-ray image. The device 10 comprises an input unit 12 and a processing unit 16. The input unit 12 is configured to provide an actual 2D X-ray image 18 of a region of interest related to a portion of a patient's body (as shown in FIG. 2 and FIG. 3). A target location 22 (as shown in FIG. 2 and FIG. 3) lies within the region of interest. At least a portion 20 of an interventional device is arranged in the region of interest. The input unit 12 is further configured to provide actual 3D ultrasound data of at least a part of the region of interest and at least the portion 20 of the interventional device 19. The target location 22 lies within the region of interest. The processing unit 16 is configured to register the actual 3D ultrasound data to the actual 2D X-ray image 18. The processing unit 16 is configured to identify the target location 22 in the 3D ultrasound data, and to determine, based on the actual 3D ultrasound data, a spatial relation between the portion 20 of the interventional device 19 and the target location 22. The processing unit 16 is configured to retrieve a distance value in a projection direction of the actual 2D X-ray image from the spatial relation. The processing unit 16 is configured to generate, based on the distance value, a graphical representation 32, for example, a coded graphical representation, indicative of the spatial relation and to be displayed with the actual 2D X-ray image 18.

In a not shown example, the processing unit 16 is configured to provide image data for displaying the actual 2D X-ray image 18 and the graphical representation 32. In an example, the portion 20 of the interventional device 19 comprises a predetermined point of the interventional device.

In an example, the region of interest is related to the portion of the patient's body in which a user that is navigating the interventional device 19.

In a further not shown example, the processing unit is configured to retrieve a distance value in a projection direction 26 (as shown in FIG. 2) of the actual 2D X-ray image from the spatial relation, and to generate the graphical representation 32 based on the distance value.

In a further not shown example, the processing unit is configured to identify and to visually indicate the target location 22 in the actual 2D X-ray image.

In a further not shown example, the target location is provided with a marker visible in the actual 3D ultrasound data.

In an example, shown as an option, a display unit 14 is provided that is configured to display the image data comprising the actual 2D X-ray image 18 and the graphical representation 32 within the actual 2D X-ray image.

In a further not shown example, a system is provided for providing spatial information of an interventional device in a live 2D X-ray image. The system comprises an X-ray imaging device, an ultrasound imaging device 36, as shown in FIG. 2 or FIG. 3, and an example of the device 10 provided for providing spatial information of an interventional device 19 in an actual 2D X-ray image 18. The X-ray imaging device provides the actual 2D X-ray image of a region of interest. The ultrasound imaging device 36 provides actual 3D ultrasound data of at least a part of the region of interest comprising at least the portion 20 of the interventional device 19.

In an example, the ultrasound imaging device 36 is insertable in a patient's body as shown in FIG. 2 and FIG. 3.

FIG. 2 shows an example of an actual 2D X-ray image 18 for a region of interest. The interventional device 19 is shown in a region of interest related to a portion of a patient's body 40 in which a user is navigating. In an example, the ultrasound device 36 is inserted in the patient's body 40. FIG. 2 further shows, the target location 22 and a graphical representation 32. In an example, the graphical representation 32 comprises visualizing a first circle 38 for the target location 22 in the 2D X-ray image. By this, the user is provided with two types of information. First, the user is provided with information of the target location 22 in the actual 2D X-ray image. Second, based on the graphical representation 32, the user is provided with the depth information of the target location. The graphical representation can be defined as such as it changes for example its color code depending on the distance value between the portion 20 of the interventional device 19 and the target location 22.

FIG. 3 shows the target location 22 visually indicated in the actual 2D X-ray image 18 with a similar graphical representation, but without a graphical representation 32, i.e. distance coding.

In an example, the first circle 38 is a point and/or a circle or another graphical symbol with a neutral color. Further, a second circle 42 (or another graphical symbol) is also visualized in the 2D X-ray image. Now, the second circle 42 shows the graphical representation 32 with a color code depending on the distance value between the portion 20 of the interventional device 19 and the target location 22.

In an example, the second circle 42 follows the movement of the portion 20 of the interventional device 19 in the actual 2D X-ray image 18. The change of the actual position of the portion 20 of the interventional device 19 relates to a movement of the portion 20.

The choice of the graphical representation could be, for example, orange when the tool is too close, and blue when it is too far, and green when tool and target are aligned in depth direction, i.e. in projection direction of the X-ray image.

In an example, the feeling of depth could furthermore be increased by additional visualization techniques, such as size change, blurring and transparency, which would have more "soft" transitions than color. Other visualization techniques are also provided.

In an example (not shown), the distance value, e.g. distance information, between the portion of the interventional device and the target location is visualized in a numerical form in the actual 2D X-ray image. Numerical form can also refer to measurement units like mm, cm, etc. In an example, the visualization of the distance value in numerical form could be arranged in the actual 2D X-ray image close to the target location, e.g. next to the first circle 38 or the second circle 42.

In one example, the distance value is related to the distance between the portion of the interventional device and the target location in projection direction, i.e. the relative distance or a distance (vector) component.

In another example, the distance value is related to the spatial distance between the portion of the interventional device and the target location, i.e. the actual or absolute distance.

Figure 4:
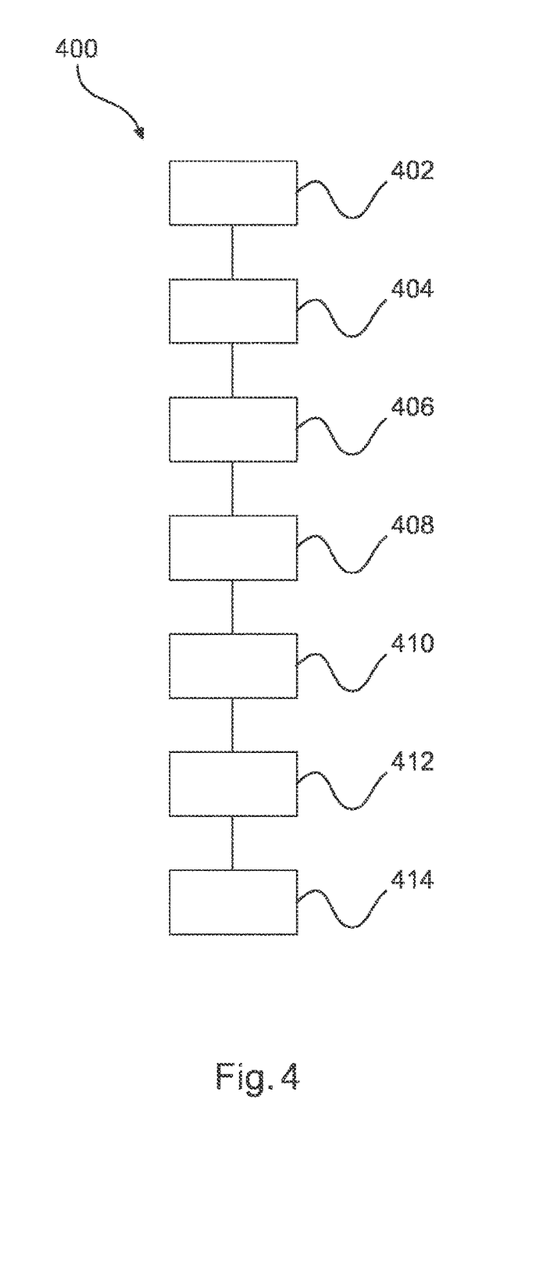
FIG. 4 shows an example of the method for providing spatial information of an interventional device in a live 2D X-ray image.

FIG. 4 illustrates a corresponding method 400 for displaying spatial information of an interventional device in a live 2D X-ray image. The method comprises the following steps. In a first step 402, also referred to as step a), an actual 2D X-ray image of a region of interest is provided, wherein the region of interest is related to a portion of the patient's body, wherein a target location lies within the region of interest. At least a portion of an interventional device is arranged in the region of interest. In a second step 404, also referred to as step b), actual 3D ultrasound data of at least a part of the region of interest and at least the portion of the interventional device is provided. In a third step 406, also referred to as step c1), the actual 3D ultrasound data is registered to the actual 2D X-ray image. In a fourth step 408, also referred to as step c2), the target location in the 3D ultrasound data is identified and the spatial relation between the portion of the interventional device and the target location is determined based on the actual 3D ultrasound data. Further, a distance value in a projection direction of the actual 2D X-ray image is retrieved from the spatial relation. In another step 410, also referred to as step c3), based on the distance value, a graphical representation indicative of the spatial relation to be displayed with the actual 2D X-ray image is generated.

In another step 412, provided and shown as an option only, also referred to as step d), the target location in the actual 2D X-ray image is identified and visually indicated. In another step 414, also provided as an option, also referred to as step e), image data for displaying the actual 2D X-ray image and the graphical representation is provided.

In a not further shown example, a further step is provided that comprises displaying the graphical representation at the target location.

In an example, the image data comprising the actual 2D X-ray image and the graphical representation is displayed.

In an example, the graphical representation is displayed at the target location as shown in FIG. 2.

In an example, it is provided that step 412 comprises identifying and visually indicating the position interventional device in the actual 2D X-ray image and, and it is provided a step 414 that comprises displaying the graphical representation at the position of interventional device 19, e.g. the predetermined portion or point of the interventional device 19.

In an example (not shown in detail), preferably, the graphical representation follows a change of the position of the interventional device within the actual 2D X-ray image.

In an example, step 414 further comprises visualizing the distance value between the interventional device 19 and the target in a numerical form in the 2D X-ray image.

Figure 5:
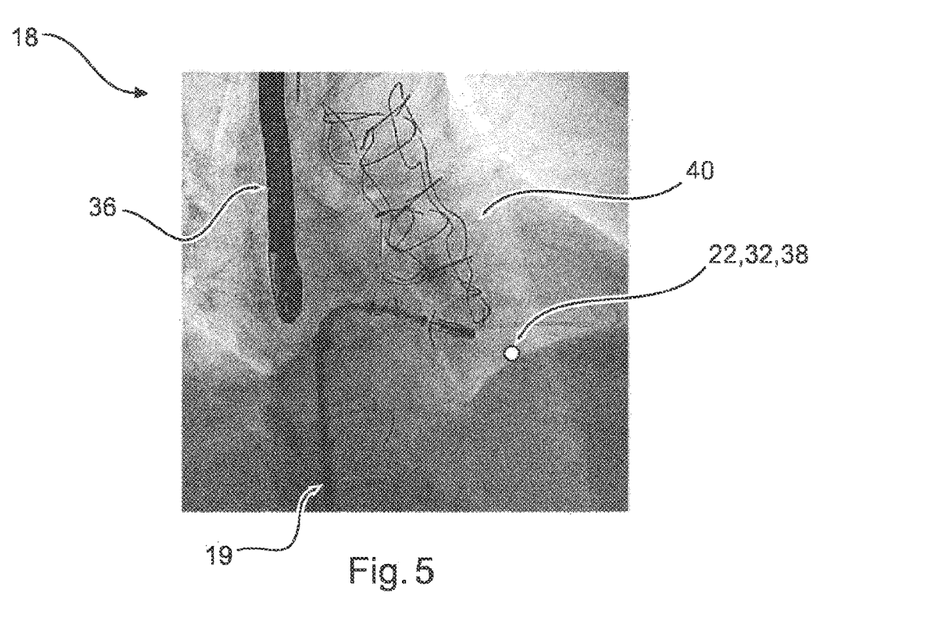
FIG. 5 shows a photographic illustration of FIG. 2.
Figure 6:
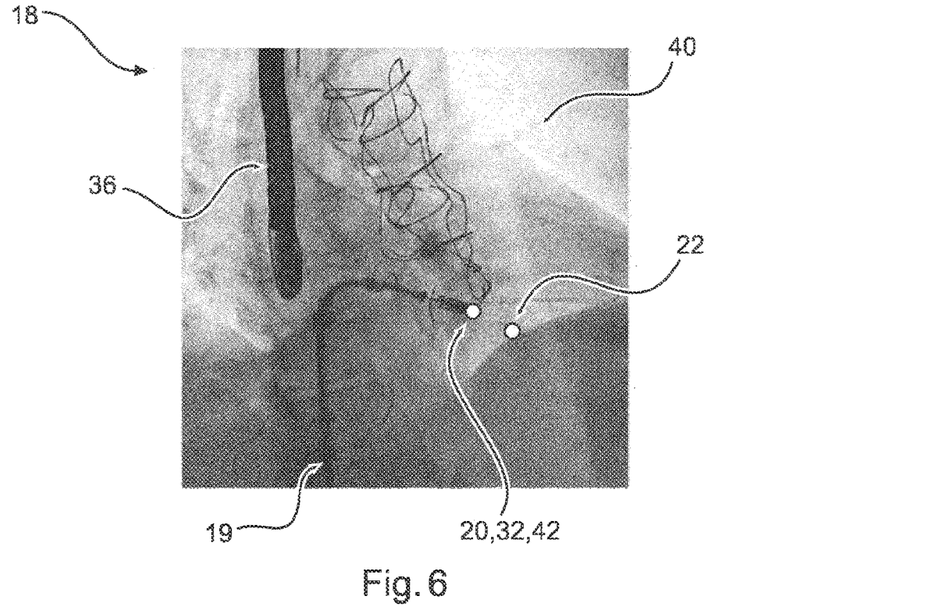
FIG. 6 shows a photographic illustration of FIG. 3.

FIG. 5 shows a photographic illustration of FIG. 2; FIG. 6 shows a photographic illustration of FIG. 3. The photographic illustration shows the gray shadows of the captured image by the X-ray imaging device.

As stated above the, circle 38 and respectively 42 changes the color coding to a color code. As a result, the relative depth of the point 20 of the interventional device 19 and the target location 22 is shown well accentuated on the captured image.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for providing spatial information of an interventional device in a live 2D X-ray image, the device comprising:
    an input unit configured to:
        provide an actual 2D X-ray image of a region of interest related to a portion of a patient's body, wherein a target location lies within the region of interest, and wherein at least a portion of an interventional device is arranged in the region of interest, and
        provide actual 3D ultrasound data of at least a part of the region of interest and at least the portion of the interventional device; and
    a processing unit configured to:
        register the actual 3D ultrasound data to the actual 2D X-ray image,
        identify the target location in the actual 3D ultrasound data,
        determine, based on the actual 3D ultrasound data, a spatial relation between the portion of the interventional device and the target location,
        retrieve a distance value in a projection direction of the actual 2D X-ray image from the spatial relation, and
        based on the distance value, generate a graphical representation indicative of the spatial relation, the graphical representation to be displayed with the actual 2D X-ray image.

2. The device according to claim 1, wherein the distance value in the projection direction of the actual 2D X-ray image is a distance value in a z-direction of the actual 2D X-ray image.

3. The device according to claim 1, wherein the processing unit is configured to generate image data comprising the actual 2D X-ray image and the graphical representation within the actual 2D X-ray image.

4. The device according to claim 1, wherein the graphical representation is a color or pattern coded graphical representation; and
    wherein the coded graphical representation is indicative of:
    i) a certain relative distance, comprising one of the group of:
    i1) too close towards or too far away from the target location, or i2), in a viewing direction of the X-ray projection, behind or in front of a plane in which the target is arranged; or
    ii) a certain absolute distance behind or in front of the plane in which the target is arranged.

5. The device according to claim 1, wherein a display unit is provided, which is configured to display image data comprising the actual 2D X-ray image and the graphical representation within the actual 2D X-ray image.

6. The device according to claim 1, wherein the processing unit is configured to identify and to visually indicate the target location in the actual 2D X-ray image.

7. The device according to claim 1, wherein the target location is provided with a marker visible in the actual 3D ultrasound data, and the processing unit is configured to identify the target location in the actual 3D ultrasound data based on the marker.

8. An X-ray imaging system comprising:
    the device according to claim 1;
    an X-ray imaging device configured to provide the actual 2D X-ray image; and
    an ultrasound imaging device configured to provide the actual 3D ultrasound data.

9. The system according to claim 8, wherein the ultrasound imaging device is insertable in a patient's body.

10. A method for providing spatial information of an interventional device in a live 2D X-ray image, the method comprising:
    providing an actual 2D X-ray image of a region of interest related to a portion of a patient's body, wherein a target location lies within the region of interest, and wherein at least a portion of an interventional device is arranged in the region of interest;
    providing actual 3D ultrasound data of at least a part of the region of interest and at least the portion of the interventional device;
    registering the actual 3D ultrasound data to the actual 2D X-ray image;

identifying the target location in the actual 3D ultrasound data;
   determining, based on the actual 3D ultrasound data, a spatial relation between the portion of the interventional device and the target location;
   retrieving a distance value in a projection direction of the actual 2D X-ray image from the spatial relation; and
generating, based on the distance value, a graphical representation indicative of the spatial relation to be displayed with the actual 2D X-ray image.

11. The method according to claim 10, further comprising: displaying the graphical representation at the target location.

12. The method according to claim 10, further comprising:
identifying and visually indicating a position of the interventional device in the actual 2D X-ray image; and
displaying the graphical representation at the position of the interventional device,
wherein the graphical representation follows a change of the position of the interventional device within the actual 2D X-ray image.

13. The method according to claim 10, further comprising: visualizing the distance value between the interventional device and the target location in a numerical form on the 2D X-ray image.

14. A non-transitory computer-readable storage medium having stored a computer program comprising instructions for controlling an apparatus, the instructions, when executed by a processing unit, cause the processing unit to:
provide an actual 2D X-ray image of a region of interest related to a portion of a patient's body, wherein a target location lies within the region of interest, and wherein at least a portion of an interventional device is arranged in the region of interest;
provide actual 3D ultrasound data of at least a part of the region of interest and at least the portion of the interventional device;
register the actual 3D ultrasound data to the actual 2D X-ray image;
identify the target location in the actual 3D ultrasound data;
determine, based on the actual 3D ultrasound data, a spatial relation between the portion of the interventional device and the target location;
retrieve a distance value in a projection direction of the actual 2D X-ray image from the spatial relation; and
generate, based on the distance value, a graphical representation indicative of the spatial relation to be displayed with the actual 2D X-ray image.

* * * * *